United States Patent [19]
Paulik et al.

[11] Patent Number: 5,117,046
[45] Date of Patent: May 26, 1992

[54] PREPARATION OF ALKYLIDENE DIESTERS

[75] Inventors: Frank E. Paulik; Robert G. Schultz, both of St. Louis, Mo.

[73] Assignee: Monsanto Company, St. Louis, Mo.

[21] Appl. No.: 591,919

[22] Filed: Jun. 30, 1975

[51] Int. Cl.$^5$ .................. C07C 67/36; C07C 67/37; C07C 69/16
[52] U.S. Cl. .................. 560/232; 560/263; 562/517; 562/607; 562/891
[58] Field of Search ............. 260/491, 496; 560/232

[56] References Cited

U.S. PATENT DOCUMENTS 3,769,329  10/1973  Paulik et al. ............ 260/496
3,772,380  11/1973  Paulik et al. ............ 260/496

Primary Examiner—Vivian Garner
Attorney, Agent, or Firm—W. Brooks

[57] ABSTRACT

Alkylidene diesters such as ethylidene diacetate are produced by reacting an ether and/or an ester under substantially anhydrous conditions with carbon monoxide and hydrogen in contact with a catalyst system comprising a rhodium compound and a halogen component at a temperature in the range from 125° to 300° C. and at a carbon monoxide partial pressure in the range from about 1.0 to 1100 kg/cm$^2$. When ethylidene diacetate is the product, it can then be decomposed to produce vinyl acetate and acetic acid by well-known techniques. Since one mole of acetic acid is also produced in the synthesis of the diacetate, the invention makes possible an overall process for the production of vinyl acetate which produces acetic acid rather than consumes it.

21 Claims, No Drawings

PREPARATION OF ALKYLIDENE DIESTERS

BACKGROUND OF THE INVENTION

The present invention relates to a new process for the production of alkylidene diesters and more particularly, to the production of ethylidene diacetate which is readily convertible to vinyl acetate.

It is known to produce vinyl esters of the type having the general formula

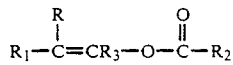

in which R, $R_1$ and $R_3$ may be either hydrogen or alkyl and $R_2$ is an alkyl group. The oldest commercial process for producing vinyl acetate, the most important of these esters, for example, involves the reaction of acetaldehyde and acetic anhydride to produce ethylidene diacetate which is then catalytically decomposed to give vinyl acetate. Because of the high cost of producing the acetic anhydride starting material, however, most vinyl acetate now made commercially is produced by processes which start with either ethylene or acetylene and with acetic acid. A method has now been discovered whereby the ethylidene diacetate can be produced directly from more readily available raw materials than those of the prior art. The diester can then be catalytically cracked to the vinyl ester providing an overall process having the advantage that for every mole of vinyl ester produced, two moles of acetic acid are simultaneously produced, one in the synthesis of the diester and one in its conversion, and no acetic acid is consumed in the process.

SUMMARY OF THE INVENTION

According to the invention, alkylidene diesters are produced by contacting an ether and/or an ester with carbon monoxide and hydrogen in the presence of a catalyst system comprising a rhodium compound and a halogen component. The halogen component may be iodine, bromine, or an iodide or a bromide. The contacting is carried out under substantially anhydrous conditions at a temperature in the range of from about 125° C. to about 300° C. and at a carbon monoxide partial pressure in the range from about 1.0 to about 1100 kg/cm². The alkylidene diester, if desired, can then be decomposed to the corresponding vinyl ester by methods well known in the art.

DESCRIPTION OF THE PREFERRED EMBODIMENTS

Suitable feedstocks that can be utilized in this invention to produce alkylidene diesters are compounds which contain an ether group

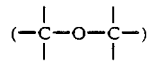

or an ester group

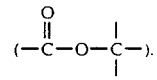

Generally these suitable feed materials can be represented by the structural formulas

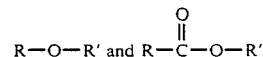

wherein R and R' are saturated aliphatic hydrocarbon groups containing from 1 to 5 carbon atoms each. Mixtures of such ethers and esters can also be used as feed materials. Non-limiting examples of suitable ether reactant materials that can be utilized in the process of the invention include dimethyl ether, diethyl ether, methyl ethyl ether, diisobutyl ether, ethyl propyl ether, amyl ether and the like. Non-limiting examples of suitable ester reactants utilized in the invention are methyl acetate, ethyl acetate, methyl propionate, ethyl propionate, butyl acetate, methyl butyrate and the like.

The carbonylation reaction of the present invention is preferably carried out by contacting the feedstock in the liquid phase with gaseous carbon monoxide and hydrogen in a liquid reaction medium containing the catalyst system such as, e.g., $RhCl_3$ and a halogen-containing promoting component such as methyl iodide, under the aforementioned suitable conditions of temperature and pressure. Alternatively, all the reactants may be in the vapor phase and these can be conducted over the solid catalyst supported on a carrier material. The particular conditions selected are the same whether the feed component is charged as vapor or liquid. The temperature will be in the range of 125° C. to 300° C. with the preferred range being 160° C. to 210° C. Especially preferred temperatures lie in the range from 165° to 190° C. While, as would be expected, increasing temperature increases the rate of reaction, at temperatures around 205° C. there is some evidence of catalyst decomposition. Also, there is a decrease in the ester/anhydride ratio and in the amount of ester produced as temperature is increased. Methane production is also increased at higher temperatures.

Partial pressures of the carbon monoxide-hydrogen mixture of the order of 1.0 kg/cm² to 1100 kg/cm² may be employed; however, the partial pressure of the mixture preferred is from 1.5 to 225 kg/cm² whereas an even more preferred range is from about 35 to 55 kg/cm². Higher pressures may be used if desired under proper conditions. However, such pressures are rarely used because high reaction rates with good product yields can be obtained by operating at the lower pressures without danger of catalyst decomposition thus providing important economic advantages over prior art methods for producing the alkylidene diesters.

A typical carbonylation reaction selective to the diester requires at least one mole of carbon monoxide per mole of ester feed. When an ether is employed as feed material, the stoichiometric mole ratio of 2 moles of carbon monoxide per mole of ether is required. Excess of carbon monoxide over the aforesaid stoichiometric amounts, however, may be present. Carbon monoxide streams containing inert impurities such as carbon dioxide, methane, nitrogen, paraffinic hydrocarbons having from 1 to 4 carbon atoms may be employed, if desired, from an available gas plant stream; however, in such cases, total reactor pressure will have to be increased to maintain a desired carbon monoxide partial pressure. Carbon monoxide concentration in the feed gas mixture may range from 1 to 100% but preferably, over 10% by volume of carbon monoxide should be present.

The key variable to achieve high diester levels is the quantity of hydrogen present. The stoichiometric ratio suggested by the chemistry of the ester reaction is a $CO/H_2$ mole ratio of 2:1 and of the ether reaction is 4:1. Amounts of hydrogen in the range from 5 mole % to 40 mole %, however, can be used. Preferred amounts are in the range from 20 to 40 mole % for the ester reaction and from 15–30 mole % for the ether reaction. In the production of ethylidene diacetate, acetic anhydride is produced along with the ethylidene diacetate when less than the theoretical amount of hydrogen is employed, the ethylidene diacetate-acetic anhydride ($EDA/Ac_2O$) ratio varying as the amount of hydrogen varies. Methane make, resulting from the side reactions $$CH_3I + H_2 \rightarrow CH_4 + HI$$

$$CH_3CHO \rightarrow CH_4 + CO,$$

increases with increasing hydrogen levels and under high hydrogen conditions, considerable $H_2$ consumption occurs so that its reactor partial pressure is drastically reduced.

The liquid reaction medium employed may include any solvent compatible with the catalyst system and may include pure ether or ester or mixtures of ether and ester feedstocks and/or the desired alkylidene diester.

For purposes of the present invention the catalyst system essentially includes a rhodium compound and a halogen component in which the halogen component is either bromine, iodine, a bromine compound or an iodine compound. Generally, the rhodium compound of the catalyst system of the present invention is believed to be present in the form of a coordination compound of rhodium with at least one of the ligands of such coordination compound provided by halogen ligands, carbon monoxide ligands, phosphine ligands, arsine ligands, stibine ligands, tin ligands, and the like. Generally, it is preferred that the catalyst system contain as a promoting component, an excess of halogen over that present as ligands in the rhodium coordination compound. The terms "coordination compound" and "coordination complex" used throughout this specification mean a compound or complex formed by combination of one or more electronically rich molecules or atoms capable of independent existence with one or more electronically poor molecules or atoms, each of which may also be capable of independent existence.

The essential rhodium compound and the halogen component of the catalyst system of the present invention may be provided by introducing into the reaction zone a coordination compound of rhodium containing halogen ligands or they may be provided by introducing into the reaction zone separately a rhodium compound and a halogen compound. The rhodium compound can be provided by any material that will produce rhodium ions. Among the materials which may be charged to the reaction zone to provide the rhodium compound of the catalyst system of the present invention are rhodium metal, rhodium salts, rhodium oxides, rhodium carbonyl compounds, organorhodium compounds, coordination compounds of rhodium and the like. Specific examples of materials capable of providing the rhodium constituent of the catalyst system of the present invention may be taken from the following non-limiting partial list of suitable materials.

| | |
|---|---|
| $RhCl_3$ | $[(n\text{-}C_4H_9)_4N][Rh(CO)_2X_2]$ where $X = Cl^-, Br^-, I^-$ |
| $RhBr_3$ | $[(n\text{-}C_4H_9)_4As]_2[Rh_2(CO)_2Y_4]$ where $Y = Br^-, I^-$ |
| $RhI_3$ | $[(n\text{-}C_4H_9)_4P][Rh(CO)I_4]$ |
| $RhCl_3 \cdot 3H_2O$ | $Rh[(C_6H_5)_3P]_2(CO)Br$ |
| $RhBr_3 \cdot 3H_2O$ | $Rh[(n\text{-}C_4H_9)_3P]_2(CO)Br$ |
| $Rh_2(CO)_4Cl_2$ | $Rh[(n\text{-}C_4H_9)_3P]_2(CO)I$ |
| $Rh_2(CO)_4Br_2$ | $RhBr[(C_6H_5)_3P]_3$ |
| $Rh_2(CO)_4I_2$ | $RhI[(C_6H_5)_3P]_3$ |
| $[Rh(CO)I_4]Na$ | $[Rh(CO)Br_4]Na$ |
| $Rh_2(CO)_8$ | $RhCl[(C_6H_5)_3P]_3$ |
| $Rh[(C_6H_5)_3P]_2(CO)I$ | $RhCl[(C_6H_5)_3P]_3H_2$ |
| $Rh[(C_6H_5)_3P]_2(CO)Cl$ | $[(C_6H_5)P]_3Rh(CO)H$ |
| Rh metal | $Rh_2O_3$ |
| $Rh(NO_3)_3$ | $Li[Rh(CO)_2I_2]$ |
| $RhCl[(C_6H_5)_3P]_2(CH_3I)_2$ | $[Rh(C_2H_4)_2Cl]_2$ |
| $Rh(SnCl_3)[(C_6H_5)_3P]_3$ | $K_4Rh_2Cl_2(SnCl_3)_4$ |
| $RhCl(CO)[(C_6H_5)_3As]_2$ | $K_4Rh_2Br_2(SnBr_3)_4$ |
| $RhI(CO)[(C_6H_5)_3Sb]_2$ | $K_4Rh_2I_2(SnI_3)_4$ |
| $Na[Rh(CO)_2I_2]$ | $[Rh(CO)_2I_2]K$ |

With those materials listed above as capable of providing the rhodium component which do not contain a halogen component from the group consisting of bromine and iodine, it will be necessary to introduce into the reaction zone such a halogen component. For example, if the rhodium component introduced is rhodium metal or $Rh_2O_3$, it will be necessary to also introduce a halide component such as methyl iodide, hydrogen iodide, iodine and the like.

Rhodium precursor materials that can be utilized to produce the rhodium compounds useful in our invention are almost limitless. The only requirement is that the rhodium precursor material is capable of producing rhodium ions. The rhodium ions can, of course, be generated in a separate catalyst preparation step or they can be generated from the rhodium precursor material in situ in the reactor utilized in our process.

As noted above, while the halogen component of the catalyst system may be in combined form with the rhodium, as for instance, as one or more ligands in a coordination compound of rhodium, it generally is preferred to have an excess of halogen present in the catalyst system as a promoting component. By excess is meant an amount of halogen greater than two atoms of halogen per atom of rhodium in the catalyst system. This promoting component of the catalyst system consists of a halogen and/or halogen compound such as hydrogen halide, alkyl- or aryl halide, metal halide, ammonium halide, phosphonium halide, arsonium halide, stibonium halide and the like. The halogen of the promoting component may be the same or different from that already present as ligands in the coordination compound of rhodium. Iodine and iodine compounds are the preferred halogen components used in our invention. While the bromine or iodine components used in our invention may be in combined form with the rhodium, as for instance, one or more ligands in a complex or coordination compound of the rhodium, it is generally preferred to charge the iodine or bromine component to the catalyst preparation zone or the reactor separately. The bromine or iodine component utilized in our invention can be provided by many different iodine or bromine precursor materials. Suitable precursor materials include bromine, iodine, any bromide compound or any iodide compound. Accordingly, suitable halogen providing or promoting components may be selected from the following non-limiting list of halogen and/or halogen-containing compounds.

| | | |
|---|---|---|
| RX | where R = any alkyl- or aryl- group where X = Br or I | e.g., $CH_3I$, $C_6H_5Br$, $CH_3CH_2I$, etc. |
| $X_2$ or $X_3^-$ | where X = Br or I | e.g., $Br_2$, $I_2$, $I_3^-$, etc. |
| HX | where X = Br or I | e.g., HBr, HI |
| RCX $\parallel$ O | where R = any alkyl- or aryl- group and X = Br or I | e.g., $CH_3CI$, etc. $\parallel$ O |
| $R_4MX$, $R_4MX_3$, or $R_3MX_2$ | where R = any alkyl- or aryl- group M = N, P, As, or Sb X = Br or I | e.g., $(C_4H_9)_4NI$ $(C_6H_5)_3PI_2$ and/or combinations of R, M, and X |

Other non-limiting examples of such compounds of bromine and iodine include ethyl iodide, ethyl bromide, benzyl iodide, benzyl bromide, sodium iodide, sodium bromide, potassium iodide, potassium bromide, lithium iodide, lithium bromide, barium iodide, magnesium iodide, calcium iodide, 1-decyl iodide, 1-decyl bromide and the like.

Although any amount of the promoting component of the catalyst system of the present invention may be employed, the amount employed is such as to produce a ratio of atoms of halogen to atoms of rhodium in the catalyst system of from above 2:1 to 50,000:1 and higher. However, the preferred ratio is 5:1 to 5,000:1 halogen atoms per rhodium atom. A more preferred ratio of halogen atoms to rhodium atoms is 10:1 to 2500:1.

The active rhodium-containing catalyst system is preferably employed in the form of a catalyst solution. The solution can also include liquid reactants, products and mixtures thereof which function as solvent or reaction media. The catalyst solutions essentially comprised of (1) the reactant feed component-product diester medium, (2) a rhodium compound and (3) a halogen component, generally in excess of the rhodium as hereinbefore set forth, may be further modified by the addition of a high-boiling inert solvent as a further component. Such an inert solvent should have a boiling point enough higher (S.T.P.) than the product diester to permit easy separation. A boiling point difference of 25° C. or more is preferred. Inert solvents within the present category include paraffin and cycloparaffin hydrocarbons of from 10 to 30 carbon atoms, aromatic hydrocarbons of from 10 to 40 carbon atoms, tertiary amines of 6 to 20 carbon atoms, amides of 4 to 20 carbon atoms, organic acids of from 2 to 20 carbon atoms, and esters and anhydrides of the aforesaid acids, heterocyclic aromatic compounds of 5 to 20 carbon atoms, as well as the chlorine, bromine and iodine-containing derivatives of all of the above said solvents. The following list exemplifies such solvents: dodecane, hexadecane, tetralin, acetic acid, acetic anhydride, octanoic acid, benzoic acid, decalin, N-methyl pyrrolidone, and the like. An especially suitable solvent is 1-methylnaphthalene since it provides for catalyst recycle with a minimum loss in catalyst activity.

The reaction rate is dependent upon catalyst concentration and temperature. Concentrations of the rhodium-containing component of the catalyst system in the liquid phase between $10^{-6}$ mole per liter and $10^{-1}$ mole per liter are normally employed with the preferred range being $10^{-4}$ mole/liter to $10^{-2}$ mole/liter. Higher concentrations even to the extent of 1 mole/liter may, however, be used if desired.

Palladium salts appear to function as co-catalysts since their addition to the system has a significant effect on the $EDA/Ac_2O$ ratio. Suitable salts for use as co-catalysts include but are not limited to palladium chloride, palladium acetate, palladium iodide, palladium acetyl acetonate and the like. The amount of the palladium salt employed may vary from about 0.1 to about 10 times the amount of the rhodium compound of the catalyst system and preferably is from about 0.25 to about 4 times the amount of the rhodium compound employed.

In addition to the above-mentioned inert solvents that can be added to the reaction system of this invention, it has been found that certain other ligands can be added to increase catalyst activity, prevent precipitation and decomposition of the catalyst system and otherwise promote the overall efficiency of the carbonylation process to produce alkylidene diesters. Such beneficial effects on both rate and $EDA/Ac_2O$ ratio maximizing have been observed in systems with low hydrogen content and those using acetic acid as solvent. Compounds which have a promoting effect on the process such as lithium acetate, quinoline, tertiary phosphines, tertiary arsines, tertiary stibines and tertiary amines can be added to the system. Non-limiting examples of the latter compounds include triphenyl phosphine, tri-n-butyl phosphine, tri-n-butyl amine, tri-n-butyl stibine, tri-n-butyl arsine and the like. The elimination of acetic acid as a solvent from the system can be effected if lithium acetate is added to the system. Amounts from 0.025 molar to 1.0 molar can be used but the preferred level is from about 0.05 molar to about 0.25 molar.

The process of the present invention is carried out under substantially anhydrous conditions. It is necessary, therefore, for suitable results to utilize ether and ester feedstocks as well as carbon monoxide and hydrogen streams that are essentially free of water. During start-up procedures for the process of the present invention, some residual water may be present in the reactor system. No substantial amounts of the alkylidene diesters will be produced until all the water has been removed from the reactor system or until all of the water has been consumed in the production of undesired by-product materials. Any conventional method for drying or dehydrating the feedstocks and reactants can be utilized to render them suitable for use in the process of the invention. As employed herein, the term "substantially anhydrous" means not more than 0.05 mole of water per mole of total ether or ester feed material present in the reactor.

The process of the present invention may be operated either as a batch or as a continuous process. In carrying out the present invention on a commercial scale, it is desirable to operate the process in a continuous mode. Such a continuous process can be very easily carried out in the liquid phase by preforming a liquid homogeneous phase that contains the rhodium component and the halogen component. For example, a rhodium component such as rhodium iodide can be added to a small amount of an inert solvent or to a small amount of the reactant material such as dimethyl ether or to a small amount of the desired product such as ethylidene diacetate. The halogen component, such as methyl iodide, can also be added to this mixture and carbon monoxide can be thereafter bubbled through the liquid mixture to preform the liquid homogeneous phase that contains the rhodium compound and the halogen component. It is desirable to include a solvent material that has a boiling point above the boiling point of the diester product to contain the rhodium compound and the halogen component. By using such a solvent component it is possible to separate the diester product from the reaction mixture without undesirable precipitation of the rhodium compound from the reaction mixture. This preformed phase can then be added to the reactor along with at least one of the reactant materials such as methyl acetate. In most instances, it is desirable to also add an additional solvent or a stabilizing component to the reaction mixture.

The reactor used in the present invention can be constructed of any suitable corrosion-resistant material and can be equipped with a gas sparger below the surface of the liquid reaction mixture. The carbon monoxide-hydrogen gas mixture can be bubbled into the liquid reaction mixture continuously. The bubbling of the gas mixture through the liquid reaction mixture provides some degree of agitation but in most instances it will be desirable to mechanically agitate the reaction mixture with paddle wheels and the like to obtain the desired contact between the carbon monoxide and the liquid phase.

A small amount of the reaction mixture can be continuously withdrawn from the reactor and passed to a separation zone. The separation zone can be a conventional simple distillation column wherein the diester product such as ethylidene diacetate can be vaporized from the reaction mixture along with any unreacted feed materials such as the methyl acetate or dimethyl ether, or other volatile materials. The remaining liquid phase, containing the rhodium compound and the halogen component can then be recycled to the reactor. In some instances, it may also be desirable to utilize a flash tank for separating the diester product and the unreacted reactants from the reaction mixture. This can be conveniently accomplished by withdrawing a portion of the reaction mixture from the reactor and passing it to the tank maintained under reduced pressure either with or without the addition of heat, thus causing the diester product and the unreacted feed components and volatile materials to vaporize, leaving the rhodium compound and the halogen component contained in the unvaporized liquid in the flash tank. This liquid in the flash tank can be recycled to the reactor. It is, of course, understood that the diester product can be further purified by conventional purification techniques that do not form a part of this invention.

Alkylidene diesters may also be produced by our invention with the feed components in the vapor phase over the rhodium-containing catalyst systems described above dispersed upon inert supports. Such a catalyst system may be in the form of a conventional fixed bed catalytic reactor. For example, dimethyl ether, methyl iodide, carbon monoxide and hydrogen, all in a vapor form, may be passed over a catalyst system consisting, for example, of $[Rh(CO)_2I]_2$ dispersed on an inert support material such as alundum, activated carbon, clay, alumina, silica-alumina, ceramic, etc., in a fixed bed reactor maintained at the temperatures and pressures, as described above, to produce ethylidene diacetate in high yields. However, use of a liquid reaction system, as discussed above with the catalyst and reactants being maintained in the liquid phase, is preferred in the process of our invention.

It will be apparent to those skilled in the art that various modifications and changes may be made in the foregoing disclosure without departing from the spirit and scope of the invention.

The following examples are presented to illustrate embodiments of the invention. However, they should not be construed as limiting the invention in any manner whatsoever.

EXAMPLE 1

A 300-ml autoclave fitted into a system allowing constant pressure and temperature reactions in which pressure drop was measured from a higher pressure reservoir was employed as the reactor. The system was designed so that a liquid could be added to the pressured-sealed autoclave. Pressure in the reservoir, autoclave temperature and differential pressure were automatically recorded. The reservoir could be repressured during the reaction to allow for reactions requiring consumption of larger amounts of CO and hydrogen. The reactor was charged first with the weighed quantities of the solid materials, e.g., a rhodium salt, then the liquid components in the desired amounts were added, e.g., the reactant methyl acetate and a solvent such as e.g., acetic acid. The autoclave was sealed and pressure-tested. At this point when methyl ether was used as reactant, it was added to the autoclave through a valved side port under pressure (3.2 kg/cm$^2$) in the acetic acid solution from a pressure bottle.

The autoclave was then pressured to 4.5–8.1 kg/cm$^2$ with a mixture of CO and H$_2$ and heated to the reaction temperature. The methyl iodide promoter for the catalyst was then added from a liquid reservoir at 36.2–50.2 kg/cm$^2$ to initiate reaction. The autoclave was pressured to the desired level with the CO-H$_2$ mixture and the reaction allowed to proceed under stirring at a rate of 750 rpm for the desired reaction period. At the end of the reaction period, the reservoir was sealed from the autoclave and cooling was begun. At 25° C., the excess pressure was vented from the autoclave and the liquid product was analyzed by gas chromatography.

Using the above-described procedure, the reactor was charged with 0.001 mole RhCl$_3 \times$ H$_2$O, 0.938 mole methyl acetate (MeOAc), 0.0172 mole acetic acid (AcOH) and 0.095 mole acetic anhydride (Ac$_2$O). The liquid reservoir contained 0.1 mole of methyl iodide (MeI). The reaction was run for 6 hours at 175° C. using an analyzed CO/H$_2$ mixture (CO—65.8 mole %, H$_2$—34.1 mole %, CO$_2$—0.1 mole %). Gas chromatographic analysis of the product showed:

| | Mole % | |
|---|---|---|
| MeI | 5.42 | |
| MeOAc | 50.34 | |
| AcOH | 26.45 | |
| Ac$_2$O | 12.21 | (4.89 mole % made in the reaction) |
| EDA | 5.57 | |

The higher pressure reservoir indicated in gas uptake of 44% of theory, and calculations indicated that 30 mole % of the MeOAc has been converted to products.

The molar ratio of reactions (to EDA and to Ac$_2$O) was calculated to be 1.14 (EDA/Ac$_2$O).

EXAMPLE 2

Using the reactor and method described in Example 1, a series of runs were made with methyl acetate as feed using various solvent systems, reaction pressures and reaction temperatures. The catalyst employed in each case was $RhCl_3 \cdot XH_2O$ (0.001 mole) with MeI promoter (0.1 mole). Conditions and results are presented in Table 1 which show temperature and pressure effects in acetic acid solvent systems. Although no solvent is necessary for the carbonylation of methyl acetate (Run 6), overall conversion is lower than that obtained when a solvent such as acetic acid, acetic anhydride or mixtures of these is present.

EXAMPLE 3

Using the reactor and method described in Example 1, a series of runs were made in which methyl acetate was reacted with a $CO/H_2$ mixture in acetic acid or acetic acid-acetic anhydride as solvent and a palladium salt was employed as a co-catalyst being added with the $RhCl_3 \cdot XH_2O$ (0.001 mole) into the reactor. Methyl iodide (0.1 mole) was employed as the halogen component of the catalyst. Reaction temperature was 175° C. and reaction pressure was 36.2 kg/cm². Conditions and results of these runs are presented in Table 2 wherein the salutary effect of addition of $PdCl_2$ as a co-catalyst on the $EDA/Ac_2O$ ratio can be seen for the preferred $CO/H_2$ ratio of 2:1.

EXAMPLE 4

Following the procedure of the previous examples, the effect of adding promoters such as lithium acetate (LiOAc), triphenyl phosphine ($P\phi_3$) and the like was determined in the reaction of methyl acetate with CO and $H_2$ using a catalyst comprising 0.001 mole $RhCl_3 \cdot XH_2O$ and 0.1 mole $CH_3I$. The reactions both with and without $PdCl_2$ co-catalyst were conducted at a temperature of 175° C. and a pressure of 36.2 kg/cm² over reaction periods varying from 3 to 6 hours. Reaction conditions and results are presented in Table 3. In addition to their beneficial effect on catalyst stability, the promoters both singly and in combination are seen to affect $EDA/Ac_2O$ ratio, conversion or both.

TABLE 1

| Run No. | $CO/H_2$ Ratio (mole %) | MeOAc (mole) | Solvent AcOH (mole) | Solvent $Ac_2O$ (mole) | Reaction Temp. (°C.) | Reaction Press. (kg/cm²) | Products, Obs. Mole % EDA | Products, Obs. Mole % $Ac_2O$ made | Mole Ratio $EDA/Ac_2O$ made | Conv. Mole % on MeOAc |
|---|---|---|---|---|---|---|---|---|---|---|
| 1 | 97.5/2.5 | 0.315 | 1.20 | — | 175 | 36.2 | — | 13.80 | — | 57 |
| 2 | 90/10 | 0.315 | 1.20 | — | 175 | 36.2 | 0.78 | 12.19 | 0.06 | 87 |
| 3 | 66/34 | 0.313 | 1.2 | — | 175 | 50.2 | 0.89 | 2.00 | 0.44 | 89.4 |
| 4 | 66/34 | 0.313 | 1.20 | — | 175 | 36.2 | 0.92 | 1.09 | 0.84 | 80.2 |
| 5 | 66/34* | 0.938 | 0.172 | 0.095 | 175 | 36.2 | 5.57 | 4.89 | 1.14 | 30 |
| 6 | 66/34 | 1.176 | — | — | 175 | 36.2 | 1.86 | 0.30 | 6.2 | 8 |
| 7 | 66/34 | 1.061 | — | 0.095 | 175 | 36.2 | 0.28 | 0** | ∞ | 0.8 |
| 8 | 66/34 | 1.053 | 0.172 | — | 175 | 36.2 | 2.06 | 2.07 | 1.0 | 5 |
| 9 | 66/34 | 0.313 | 1.2 | — | 160 | 36.2 | 1.09 | 4.12 | 0.26 | 74.6 |
| 10 | 66/34 | 0.313 | 1.2 | — | 205 | 36.2 | 3.78 | 3.99 | 0.95 | 80.0 |
| 11 | 66/34 | 0.313 | 1.2 | — | 175 | 22.1 | 0.80 | 6.31 | 0.13 | 72.8 |

*Data from Example 1 above, repeated for comparative purposes.
**Indicates net consumption of $Ac_2O$ from solution.

TABLE 2

| Run No. | $CO/H_2$ Ratio (mole %) | MeOAc (mole) | Solvent AcOH (mole) | Solvent $Ac_2O$ (mole) | Co-catalyst $PdCl_2$ (mole) | Reaction Time (hr) | Products, Obs. Mole % EDA | Products, Obs. Mole % $Ac_2O$ made | Mole Ratio $EDA/Ac_2O$ made | Conv. Mole % on MeOAc |
|---|---|---|---|---|---|---|---|---|---|---|
| 1 | 90/10 | 0.315 | 1.20 | — | — | 4 | 0.78 | 12.19 | 0.06 | 87 |
| 2 | 90/10 | 0.315 | 1.20 | — | 0.0015 | 4 | 0.48 | 12.92 | 0.04 | 76 |
| 3 | 66/34 | 0.315 | 1.20 | — | — | 3 | 1.51 | 5.37 | 0.28 | 44 |
| 4 | 66/34 | 0.315 | 1.20 | — | 0.0015 | 3 | 2.29 | 2.15 | 1.07 | 65 |
| 5 | *66/34 | 0.938 | 0.176 | 0.095 | — | 6 | 5.57 | 4.89 | 1.14 | 30 |
| 6 | 66/34 | 0.938 | 0.176 | 0.095 | 0.0015 | 6 | 4.04 | 0** | ∞ | 16 |

*Repeat of data from Example 1 for comparison.
**Indicates net consumption of $Ac_2O$ from system.

TABLE 3

| Run No. | $CO/H_2$ Ratio (mole %) | MeOAc (mole) | Solvent AcOH (mole) | Solvent $Ac_2O$ (mole) | Co-catalyst $PdCl_2$ (mole) | Promoter $P\phi_3$ (mole) | Promoter LiOAc (mole) | Products Obs. Mole % EDA | Products Obs. Mole % $Ac_2O$ made | Mole Ratio $EDA/Ac_2O$ made | Conv. Mole % on MeOAc |
|---|---|---|---|---|---|---|---|---|---|---|---|
| 1* | 66/34 | 0.938 | 0.172 | 0.095 | — | — | — | 5.57 | 4.89 | 1.14 | 30 |
| 2 | 66/34 | 0.938 | 0.172 | 0.095 | 0.0015 | — | — | 4.04 | 0** | ∞ | 16 |
| 3 | 66/34 | 0.938 | 0.172 | 0.095 | — | — | 0.010 | 7.72 | 19.79 | 0.39 | 60 |
| 4 | 66/34 | 0.938 | 0.172 | 0.095 | — | 0.0025 | — | 3.45 | 7.67 | 0.45 | 39 |
| 5 | 66/34 | 0.938 | 0.172 | 0.095 | 0.0015 | — | 0.010 | 8.02 | 1.64 | 4.88 | 53 |
| 6 | 66/34 | 0.938 | 0.172 | 0.095 | 0.0015 | 0.0025 | — | 12.05 | 5.53 | 2.18 | 66 |
| 7 | 66/34 | 0.938 | 0.172 | 0.095 | — | 0.0025 | 0.010 | 19.46 | 14.00 | 1.39 | 88 |
| 8 | 66/34 | 0.938 | 0.172 | 0.095 | 0.0015 | 0.0025 | 0.010 | 19.81 | 15.85 | 1.25 | 86 |
| 9 | 66/34 | 1.06 | — | 0.095 | 0.0015 | 0.0025 | 0.010 | 23.37 | 17.24 | 1.36 | 87 |
| 10 | 90/10 | 0.315 | 1.20 | — | — | — | — | 0.78 | 12.19 | 0.06 | 87 |
| 11 | 90/10 | 0.315 | 1.20 | — | — | 0.012 | — | 2.48 | 15.47 | 0.16 | 98 |
| 12 | 90/10 | 0.315 | 1.20 | — | — | — | 0.012 | 0.99 | 7.50 | 0.13 | 33 |

TABLE 3-continued

| Run No. | CO/H$_2$ Ratio (mole %) | MeOAc (mole) | Solvent AcOH (mole) | Solvent Ac$_2$O (mole) | Co-catalyst PdCl$_2$ (mole) | Promoter Pφ$_3$ (mole) | Promoter LiOAc (mole) | Products Obs. Mole % EDA | Products Obs. Mole % Ac$_2$O made | Mole Ratio EDA/Ac$_2$O made | Conv. Mole % on MeOAc |
|---|---|---|---|---|---|---|---|---|---|---|---|
| 13 | 90/10 | 0.315 | 1.20 | — | 0.0015 | — | — | 0.48 | 12.92 | 0.04 | 76 |
| 14 | 90/10 | 0.315 | 1.20 | — | — | 0.012 | 0.005 | 0.61 | 12.74 | 0.05 | 81 |
| 15 | 90/10 | 0.315 | 1.20 | — | 0.0015 | 0.012 | — | 4.58 | 15.54 | 0.29 | 100 |
| 16 | 66/34 | 0.315 | 1.20 | — | — | — | — | 1.51 | 5.37 | 0.28 | 44 |
| 17 | 66/34 | 0.315 | 1.20 | — | — | 0.006 | — | 4.35 | 1.30 | 3.35 | 97 |
| 18 | 66/34 | 0.315 | 1.20 | — | — | — | 0.010 | 9.25 | 1.88 | 3.00 | 87 |
| 19 | 66/34 | 0.315 | 1.20 | — | 0.0015 | — | — | 2.29 | 2.15 | 1.07 | 65 |
| 20 | 66/34 | 0.315 | 1.20 | — | — | 0.006 | 0.010 | 6.63 | 4.34 | 1.53 | 91 |
| 21 | 66/34 | 0.315 | 1.20 | — | 0.0015 | 0.006 | — | 6.31 | 0 | ∞ | 96 |
| 22 | 66/34 | 0.315 | 1.20 | — | 0.0015 | — | 0.010 | 7.49 | 1.04 | 7.20 | 97 |
| 23 | 66/34 | 0.315 | 1.20 | — | 0.0015 | 0.006 | 0.010 | 8.55 | 0 | ∞ | 98 |

*Data from Example 1 for comparison
**Indicates net consumption of Ac$_2$O from system

EXAMPLE 5

Another series of runs conducted as in the preceding examples was made in which the amount of hydrogen in the CO/H$_2$ reactant mixture was varied. The reaction system consisted of the catalyst combination of 0.001 mole RhCl$_3$·XH$_2$O and 0.1 mole of CH$_3$I, about 0.938 mole of the feed methyl acetate, 0.2 mole of acetic anhydride solvent, and 0.0015 mole PdCl$_2$, 0.012 mole of triphenyl phosphine and 0.05 mole of lithium acetate as promoters. The reaction was carried out at 175° C. and 36.2 kg/cm$^2$ over reaction periods from 5.5–7 hours. Results at the various concentrations of H$_2$ presented in Table 4 show the effect of increasing H$_2$ level on the EDA/Ac$_2$O ratio and the conversion under otherwise similar conditions and that the optimum ratio of CO to H$_2$ is about 2:1.

TABLE 4

| Run No. | CO/H$_2$ Ratio (mole %) | Products, Obs. Mole % EDA | Products, Obs. Mole % Ac$_2$O made | Mole Ratio EDA/Ac$_2$O made | Conv. Mole % on MeOAc |
|---|---|---|---|---|---|
| 1 | 95/5 | 2.82 | 50.7 | 0.056 | 90.9 |
| 2 | 90/10 | 3.25 | 46.4 | 0.070 | 90.1 |
| 3 | 80/20 | 7.08 | 36.6 | 0.19 | 86.6 |
| 4 | 66/34 | 10.39 | 14.9 | 0.69 | 75.3 |
| 5* | 66/34 | 16.32 | 0 | ∞ | 48.1 |

*0.01 mole LiOAc, no Pφ$_3$, and pressure of 43.2 kg/cm$^2$.

EXAMPLE 6

The effect of reaction temperature and pressure on the EDA synthesis from methyl acetate is evident from reactions carried out over a 3-hour period between methyl acetate (0.313 mole) and CO/H$_2$ in the optimum mole ratio (2/1) with a catalyst comprising 0.001 mole RhCl$_3$·XH$_2$O and 0.1 mole MeI and a reaction system containing 1.2 moles of acetic acid as a solvent, 0.0015 mole PdCl$_2$ as co-catalyst and 0.006 mole triphenyl phosphine and 0.010 mole lithium acetate as promoters. Results presented in Table 5 show that with the more efficient system using a co-catalyst and reaction promoters, preferred temperatures remain in the range from 160° to 210° C. and preferred pressures are from about 35 to about 55 kg/cm$^2$.

TABLE 5

| Run No. | Reaction Temp. °C. | Reaction Press. kg/cm$^2$ | Products, Obs. Mole % EDA | Products, Obs. Mole % Ac$_2$O made | Mole Ratio EDA/Ac$_2$O made | Conv. Mole % on MeOAc |
|---|---|---|---|---|---|---|
| 1 | 160 | 36.2 | 10.40 | 2.95 | 3.53 | 87.9 |
| 2 | 175 | 36.2 | 8.80 | <0.50 | 17.6 | 78.2 |
| 3 | 205 | 36.2 | 5.72 | 3.79 | 1.51 | 92.1 |
| 4 | 175 | 21.1 | 9.16 | 2.44 | 3.75 | 83.7 |
| 5 | 175 | 50.2 | 10.17 | Trace | ∞ | 96.7 |

EXAMPLE 7

The carbonylation of dimethyl ether to ethylidene diacetate was effected using the technique and apparatus described in the preceding examples. The charge to the reactor included 0.3 mole of dimethyl ether, 0.98 mole of acetic acid, 0.19 mole of acetic anhydride, 0.001 mole RhCl$_3$, 0.1 mole MeI, 0.0015 mole PdCl$_2$, and 0.01 mole LiOAc. CO-hydrogen was fed at a rate to provide a mole ratio of 4/1 of CO/H$_2$, hydrogen being maintained at about 20 mole %. Reaction temperature was about 175° C. and reaction pressure 42.2 kg/cm$^2$ over the 6-hr reaction period. A CO/H$_2$ uptake of 88% was observed and an EDA/Ac$_2$O made ratio of ∞ was found (indicating a net consumption of Ac$_2$O from the system). The product contained 0.036 mole methyl acetate, 0.145 mole acetic anhydride, 0.097 mole ethylidene diacetate.

What is claimed is:

1. A process for the production of alkylidene diesters which comprises contacting a reactant selected from the group consisting of ethers having the formula R—O—R' and esters having the formula

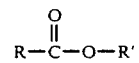

wherein R and R' are saturated aliphatic hydrocarbon groups containing from 1 to 5 carbon atoms each and mixtures of said compounds with carbon monoxide, hydrogen and a catalyst system consisting essentially of a catalyst system selected from the group consisting of (1) a rhodium compound and a halogen component selected from the group consisting of bromine, iodine, bromides and iodides,
(2) a rhodium compound, a halogen component selected from the group consisting of bromine, iodine, bromides and iodides and a palladium salt,
(3) a rhodium compound, a halogen component selected from the group consisting of bromine, iodine, bromides and iodides and a reaction promoter selected from the group consisting of tertiary phosphines, tertiary arsines, tertiary stibines, tertiary amines, quinoline, lithium acetate and mixtures thereof, and
(4) a rhodium compound, a halogen component selected from the group consisting of bromine, iodine, bromides and iodides, a palladium salt and a reaction promoter selected from the group consisting of tertiary phosphine, tertiary arsines, tertiary stibines, tertiary amines, quinoline, lithium acetate and mixtures thereof, said contacting being effected under substantially anhydrous conditions at a temperature within the range from about 125° C. to about 300° C., at a carbon monoxide partial pressure in the range from 1 to 1100 kg/cm$^2$ and with an amount of hydrogen from about 5 to about 40 mole per cent.

2. The process of claim 1 wherein said catalyst system employed consists of a rhodium compound, a halogen component selected from the group consisting of bromine iodine, bromides and iodides, and a palladium salt.

3. The process of claim 2 wherein the amount of said palladium salt is in the range from about 0.1 to about 10 times the amount of rhodium compound in said catalyst system.

4. The process of claim 1 wherein said catalyst system employed consists of a rhodium compound, a halogen component selected from the group consisting of bromine, iodine, bromides and iodides, and a reaction promoter selected from the group consisting of tertiary phosphines, tertiary arsines, tertiary stibines, tertiary amines, quinoline, lithium acetate and mixtures thereof.

5. The process of claim 1 wherein said catalyst system employed consists of a rhodium compound, a halogen component selected from the group consisting of bromine, iodine, bromides and iodides, a palladium salt and a reaction promoter selected from the group consisting of tertiary phosphines, tertiary arsines, tertiary stibines, tertiary amines, quinoline, lithium acetate and mixtures thereof.

6. The process of claim 5 wherein the reaction promoter is present in amounts from about 0.025 molar to 1.0 molar.

7. The process of claim 6 wherein said reactant is an ester, one mole of carbon monoxide is employed per mole of ester and the amount of hydrogen employed is from about 20 to about 40 mole per cent.

8. The process of claim 7 wherein said contacting is effected in a liquid reaction medium at a temperature between about 160° and 210° C. and a carbon monoxide partial pressure from about 35 to about 55 kg/cm$^2$.

9. The process of claim 8 wherein said rhodium compound of said catalyst system is selected from the group consisting of rhodium salts, rhodium oxides and rhodium carbonyls consisting only of rhodium and carbonyl moieties.

10. The process of claim 9 wherein said halogen component is an iodide.

11. The process of claim 10 wherein said ester is methyl acetate, said rhodium compound is rhodium trichloride, said iodide is methyl iodide, said palladium salt is palladium chloride and said reaction promoter is triphenyl phosphine.

12. The process of claim 10 wherein said ester is methyl acetate, said rhodium compound is rhodium trichloride, said iodide is methyl iodide, said palladium salt is palladium chloride, and said reaction promoter is lithium acetate.

13. The process of claim 10 wherein said ester is methyl acetate, said rhodium compound is rhodium trichloride, said iodide is methyl iodide, said palladium salt is palladium chloride and said reaction promoter is a mixture of triphenyl phosphine and lithium acetate.

14. The process of claim 6 wherein said reactant is an ether, two moles of carbon monoxide are employed per mole of ether and the amount of hydrogen employed is from about 15 to about 30 mole per cent.

15. The process of claim 14 wherein said contacting is effected in a liquid reaction medium at a temperature between about 160° C. and 210° C. and a carbon monoxide partial pressure from about 35 to about 55 kg/cm$^2$.

16. The process of claim 15 wherein said rhodium compound of said catalyst system is selected from the group consisting of rhodium salts, rhodium oxides and rhodium carbonyls consisting only of rhodium and carbonyl moieties.

17. The process of claim 16 wherein said halogen component is an iodide.

18. The process of claim 17 wherein said ether is dimethyl ether, said rhodium compound is rhodium trichloride, said iodide is methyl iodide, said palladium salt is palladium chloride and said reaction promoter is triphenyl phosphine.

19. The process of claim 17 wherein said ether is dimethyl ether, said rhodium compound is rhodium trichloride, said iodide is methyl iodide, said palladium salt is palladium chloride and said reaction promoter is lithium acetate.

20. The process of claim 17 wherein said ether is dimethyl ether, said rhodium compound is rhodium trichloride, said iodide is methyl iodide, said palladium salt is palladium chloride and said reaction promoter is a mixture of triphenyl phosphine and lithium acetate.

21. A process for the production of alkylidene diesters which comprises contacting a reactant selected from the group consisting of ethers having the formula ROR' and esters having the formula RCOOR' wherein R and R' are saturated aliphatic hydrocarbon groups containing from 1 to 5 carbon atoms each and mixtures of said compounds with carbon monoxide, hydrogen and a catalyst system consisting essentially of a catalyst system selected from the group consisting of:
(1) a rhodium compound and a halogen component selected from the group consisting of bromine, iodine, bromides and iodides and
(2) a rhodium compound and a halogen component selected from the group consisting of bromine, iodine, bromides and iodides and a reaction promoter selected from the group consisting of tertiary phosphines, tertiary arsines, tertiary stibines, tertiary amines, quinoline and mixtures thereof, said contacting being effected under substantially anhydrous conditions at a temperature within the range from about 125° C. to about 300° C., at a carbon monoxide partial pressure in the range from 1 to 1100 Kg/cm$^2$ and with an amount of hydrogen from about 5 to about 40 mole %.

* * * * *